US00PP22589P3

(12) United States Plant Patent
Larson et al.

(10) Patent No.: US PP22,589 P3
(45) Date of Patent: Mar. 20, 2012

(54) STRAWBERRY PLANT NAMED 'MOJAVE'

(50) Latin Name: ***Fragaria×ananassa* Duch.**
Varietal Denomination: Mojave

(75) Inventors: Kirk D. Larson, Santa Ana, CA (US); Douglas V. Shaw, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 273 days.

(21) Appl. No.: 12/657,867

(22) Filed: Jan. 29, 2010

(65) Prior Publication Data

US 2011/0191919 P1 Aug. 4, 2011

(51) Int. Cl.
*A01H 5/00* (2006.01)

(52) U.S. Cl. ..... Plt./208

(58) Field of Classification Search ..... Plt./208
See application file for complete search history.

(56) References Cited

U.S. PATENT DOCUMENTS

| | | | | | |
|---|---|---|---|---|---|
| PP4,538 | P | * | 5/1980 | Bringhurst et al. | Plt./209 |
| PP5,262 | P | * | 7/1984 | Voth et al. | Plt./208 |
| PP8,708 | P | * | 5/1994 | Voth et al. | Plt./209 |
| PP13,469 | P3 | * | 1/2003 | Larson et al. | Plt./208 |
| PP19,472 | P3 | * | 11/2008 | Shaw et al. | Plt./208 |

OTHER PUBLICATIONS

UPOV ROM GTITM Computer Database, GTI Jouve Retrieval Software 2011/10 Citation for 'Mojave'.*

Anonymous. "Benecia Strawberry Plants and Mojave Strawberry Plants" Strawberry Plants.org Jun. 2, 2010 available at: http://strawberryplants.org/2010/06/benecia-strawberry-plants-mojave-strawberry-plants/.*

* cited by examiner

*Primary Examiner* — Wendy C Haas
(74) *Attorney, Agent, or Firm* — Kilpatrick Townsend & Stockton LLP

(57) ABSTRACT

'Mojave' is typical of short-day (June bearing) strawberry cultivars and produces fruit over an extended period when treated appropriately in arid, subtropical climates. When treated with appropriate planting regimes, 'Mojave' has larger fruit and produces individual-plant yields greater than that of 'Camarosa' (U.S. Plant Pat. No. 8,708). It further produces similar quantities of fruit per plant but develops larger and higher quality fruit than 'Ventana' (U.S. Plant Pat. No. 13,649). 'Mojave' also produces a larger fraction of marketable fruit than any of the comparison cultivars.

4 Drawing Sheets

Genus and species: The strawberry cultivar of this invention is botanically identified as *Fragaria×ananassa* Duch.

Variety denomination: The variety denomination is 'Mojave'.

BACKGROUND OF THE INVENTION

This invention relates to a new and distinctive short-day type cultivar designated as 'Mojave'. This new cultivar was the result of a cross performed in 2004 between the cultivar 'Palomar' (U.S. Plant Pat. No. 19,472) and unreleased germplasm accession Cal 1.57-601 (unpatented). Accession Cal 1.57-601 was chosen as a parent due to its large, dark colored, and high quality fruit and also due to its high early-season productivity. 'Mojave' was first fruited at a center near Irvine, Calif. in 2005, where it was selected, originally designated Cal 4.44-603, and propagated asexually by runners. Following selection and during testing, the plant of this selection was designated 'C227'. It was later designated 'Mojave' for the purposes of introduction into commerce. Asexual propagules from this original source have been tested at Watsonville, Calif., in Irvine, Calif., and to a limited extent in grower fields starting in 2007. The cultivar is stable and reproduces true to type in successive generations of asexual reproduction.

BRIEF SUMMARY OF THE INVENTION

'Mojave' is typical of short-day (June bearing) strawberry cultivars and produces fruit over an extended period when treated appropriately in arid, subtropical climates. When treated with appropriate planting regimes, 'Mojave' has larger fruit and produces individual-plant yields greater than that of 'Camarosa' (U.S. Plant Pat. No. 8,708). It further produces similar quantities of fruit per plant but develops larger and higher quality fruit than 'Ventana' (U.S. Plant Pat. No. 13,469). 'Mojave' also produces a larger fraction of marketable fruit than any of the comparison cultivars.

BRIEF DESCRIPTION OF THE DRAWINGS

The figures depict various characteristics of the 'Mojave' cultivar.

DETAILED DESCRIPTION OF THE INVENTION

Figure 1:
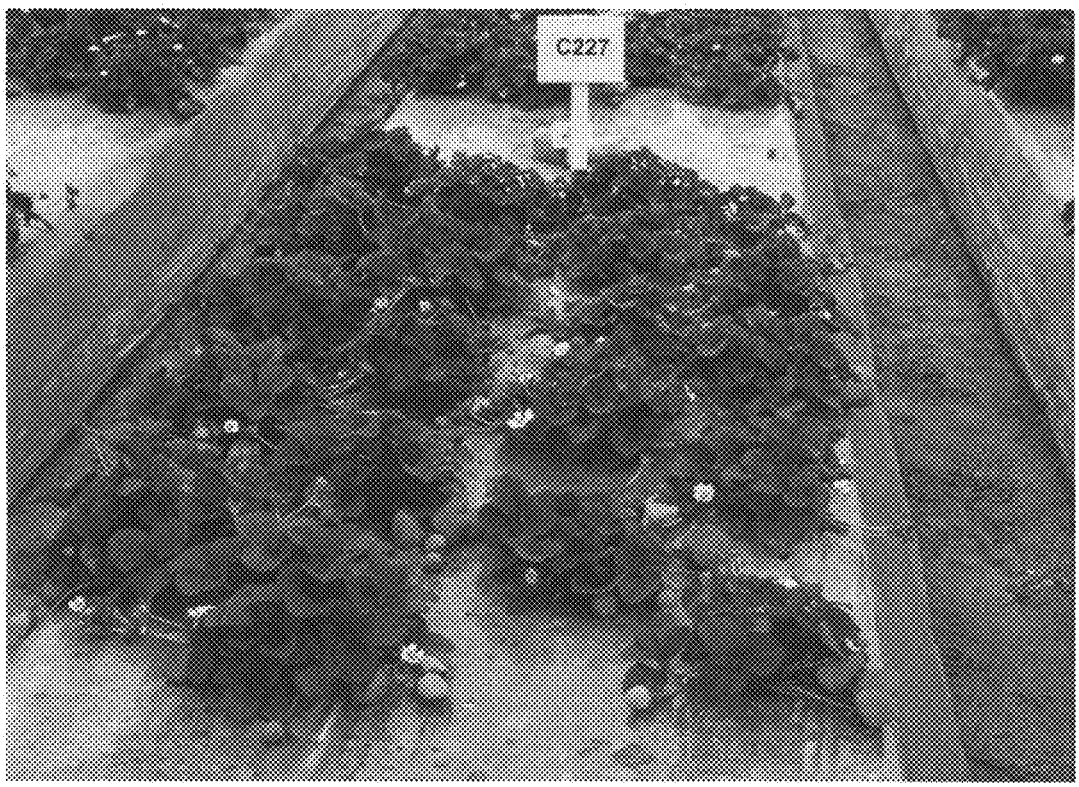
FIG. 1 shows the general flowering and fruiting characteristics of the plant in a field planting.
Figure 2:
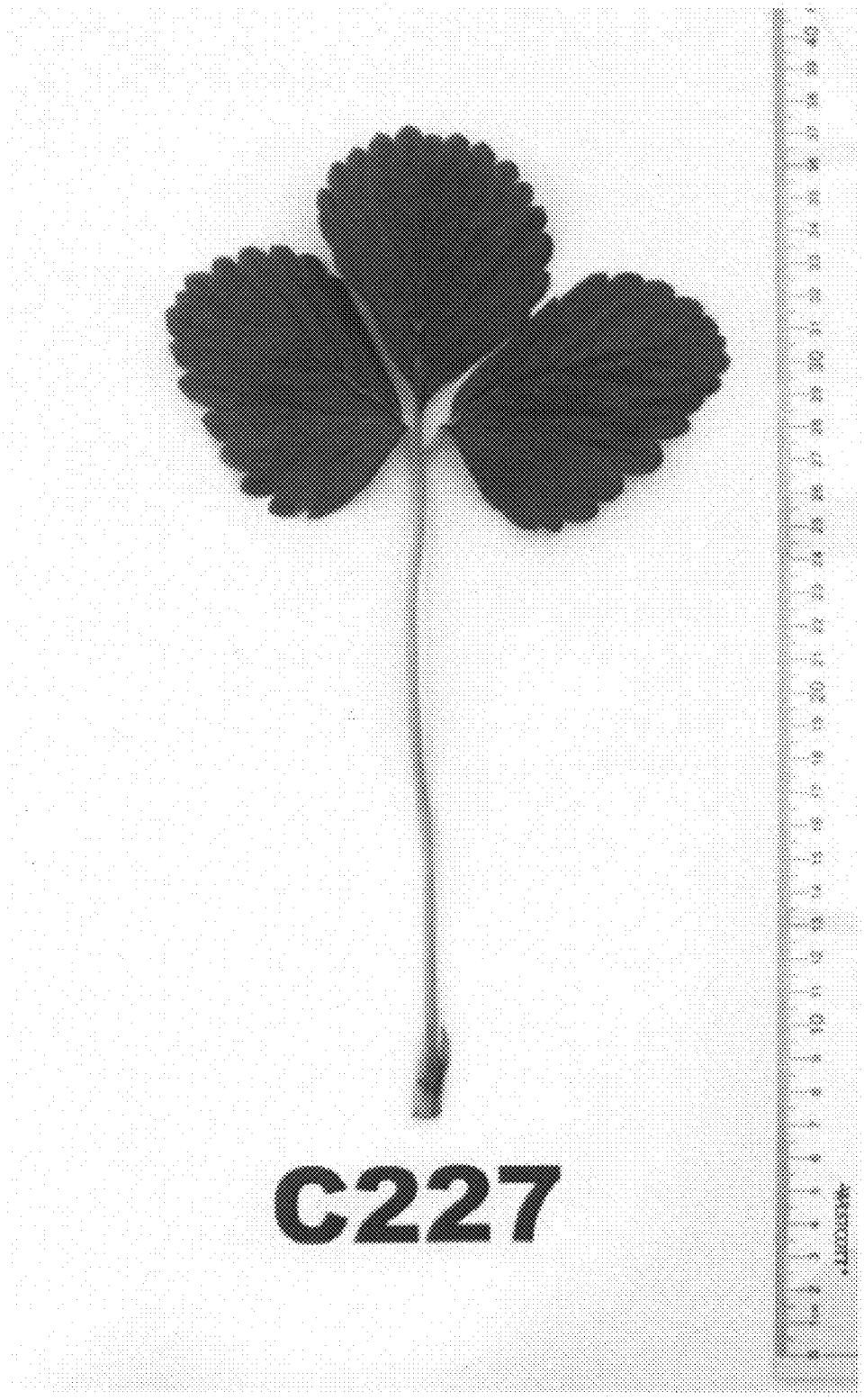
FIG. 2 shows a typical leaf at mid-season.
Figure 3:
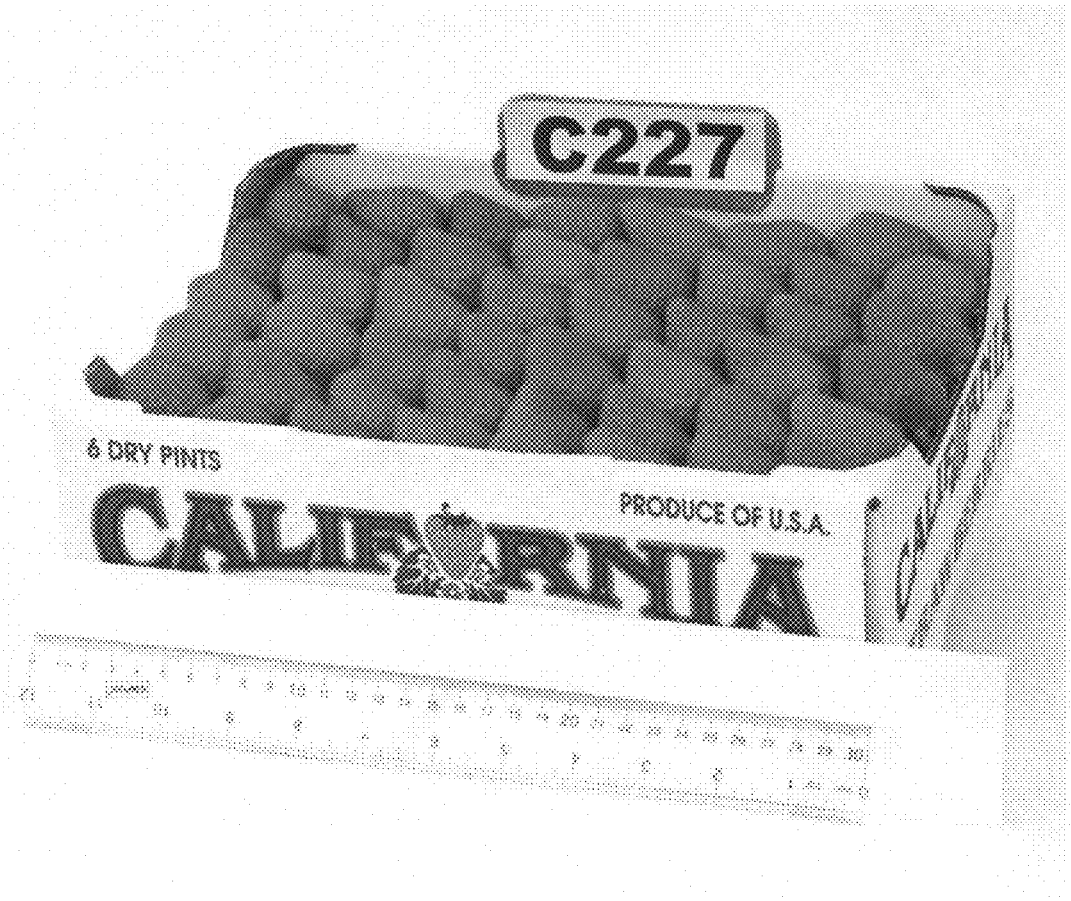
FIG. 3 shows representative mid-season fruit.
Figure 4:
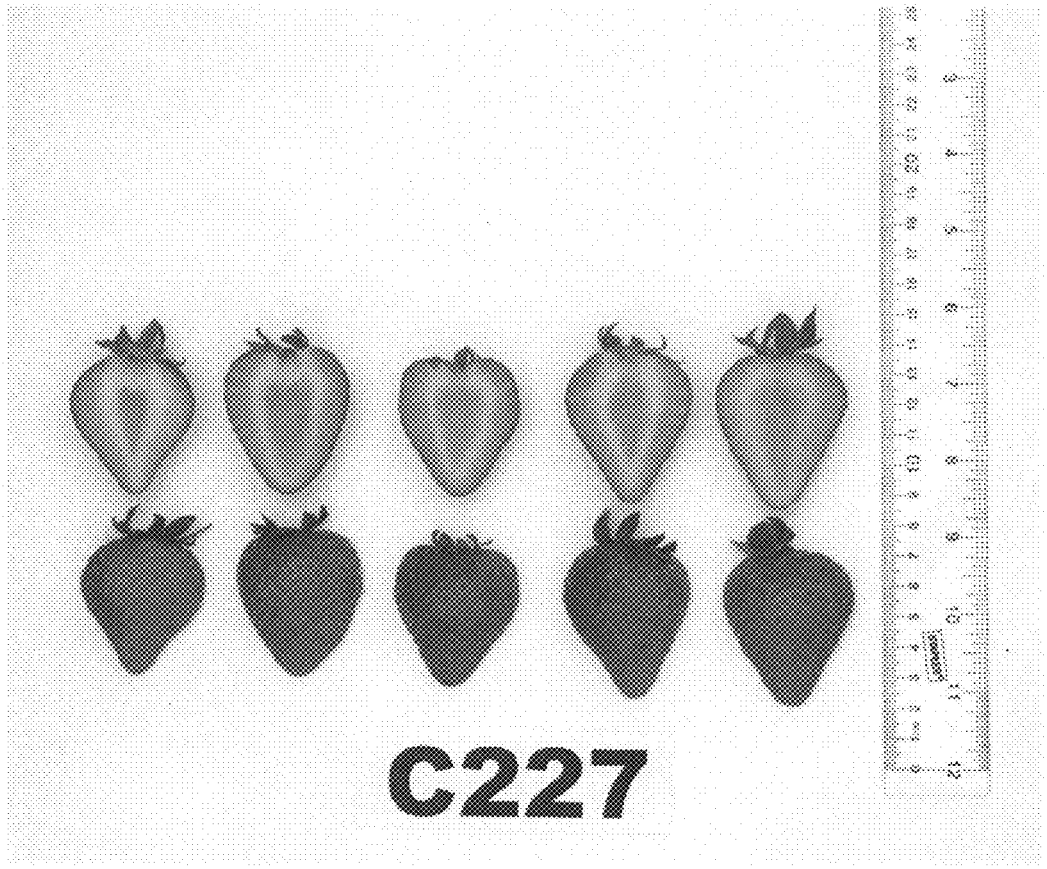
FIG. 4 shows a cross-section of representative mid-season fruit.

'Mojave' is typical of short-day strawberry cultivars and produces fruit over an extended period when treated appropriately in arid, subtropical climates. The production pattern for 'Mojave' is similar to that of 'Ventana' and 'Palomar', although it is somewhat earlier to initiate fruiting with most cultural treatments than 'Camarosa'. 'Mojave' initiates fruiting slightly later than 'Ventana' when established in late fall. 'Mojave' will be of special interest for winter plantings, where 'Camarosa', 'Ventana', and 'Palomar' have been successful, and in summer plantings where 'Pajaro' (U.S. Plant Pat. No. 4,538) and 'Chandler' (U.S. Plant Pat. No. 5,262) have been successful. Color descriptions are drawn to the Munsell Color Chart.

Plants and foliage:

Fruiting plants of 'Mojave' are similar in morphology to 'Camarosa', although slightly more open and erect and somewhat smaller than 'Ventana', throughout most of the production season with most cultural treatments. 'Mojave' plants are larger than those of 'Palomar' and similar in size to those of 'Camarosa' in most production environments. Comparative statistics for foliar characteristics near mid-season are given for 'Mojave' and three comparison cultivars in Table 1. Individual leaflets for 'Mojave' are larger than all three comparison cultivars. Leaves (including petioles) for 'Mojave' are similar in length to 'Ventana' and 'Camarosa', but with shorter petioles and larger leaflets. The leaves are longer than those for 'Palomar'. The adaxial (upper) surfaces of leaves for 'Mojave' are similar in color to 'Camarosa' and darker than 'Ventana' leaves at mid season, whereas the abaxial (lower) surface is somewhat lighter in color. Leaves of 'Mojave' have consistently more concavity than 'Camarosa', less concavity than 'Palomar' and are similar to those of 'Ventana'. 'Mojave' leaves have similar shape and number of serrations at mid season as the comparison cultivars.

TABLE 1

Foliar and plant characteristics for 'Mojave', 'Camarosa', 'Palomar', and 'Ventana'.

| | Cultivar | | | |
|---|---|---|---|---|
| Foliar Character | 'Camarosa' | 'Ventana' | 'Palomar' | 'Mojave' |
| Plant height (mm) | | | | |
| mean | 299 | 277 | 262 | 291 |
| range | 280-320 | 250-300 | 250-290 | 270-300 |
| Plant spread (mm) | | | | |
| mean | 431 | 432 | 388 | 433 |
| range | 395-490 | 370-485 | 360-455 | 400-470 |
| Mid-tier leaflet | | | | |
| Length (mm) | | | | |
| mean | 100 | 92 | 88 | 108 |
| range | 93-105 | 55-110 | 76-93 | 96-120 |
| Width (mm) | | | | |
| mean | 87 | 79 | 72 | 87 |
| range | 80-100 | 73-90 | 65-80 | 77-95 |
| Mid-tier leaf | | | | |
| Length (mm) | | | | |
| mean | 290 | 314 | 244 | 308 |
| range | 267-325 | 235-350 | 160-282 | 270-400 |
| Width (mm) | | | | |
| mean | 178 | 169 | 156 | 181 |
| range | 152-210 | 150-190 | 128-175 | 165-210 |
| Leaf components | | | | |
| Petiole length (mm) | | | | |
| mean | 194 | 220 | 169 | 201 |

TABLE 1-continued

Foliar and plant characteristics for 'Mojave', 'Camarosa', 'Palomar', and 'Ventana'.

| | Cultivar | | | |
|---|---|---|---|---|
| Foliar Character | 'Camarosa' | 'Ventana' | 'Palomar' | 'Mojave' |
| range | 170-220 | 190-240 | 150-175 | 165-245 |
| Petiole diameter (mm) | | | | |
| mean | 5.1 | 4.9 | 4.5 | 4.8 |
| range | 4-6 | 4-6 | 4-5 | 4-6 |
| Petiolule length (mm) | | | | |
| mean | 8.5 | 6.1 | 5.5 | 7.6 |
| range | 6-10 | 5-7 | 4-6 | 6-9 |
| # leaflets/leaf | 3 | 3 | 3, rarely 4 or 5 | 3 |
| Leaf convexity | Some convex, most flat to slight concave | flat to very concave | concave to very concave | |
| Serrations | | | | |
| number/leaf | 19.5 | 20.6 | 20.6 | 20.5 |
| range | 18-21 | 18-23 | 18-23 | 18-24 |
| shape | rounded, some semi-pointed | semi-pointed | semi-pointed | rounded, some semi-pointed |
| Leaf pubescence | light-moderate | light-moderate | moderate-light | moderate |
| Petiole pubescence | | | | |
| density | heavy heavy | moderate-heavy | heavy | moderate- |
| direction | perpen-dicular | perpen-dicular to acropetal | perpen-dicular | perpen-dicular |
| Petiole color (Munsell) | 2.5 GY 8/9 | 2.5 GY 8/9 | 2.5 GY 8/9 | 5 GY 8/8 |
| Stipule length (mm) | | | | |
| mean | 33.8 | 31.9 | 33.3 | 35.9 |
| range | 30-45 | 25-40 | 25-41 | 19-40 |
| Stipule color | | | | |
| core | 7.5 GY 9/4 | 2.5 GY 9/8 | 10 Y 9/9 | 2.5 GY 9/8 |
| margins | 7.5 GY 8/7 | 10 Y 8/11 | 2.5 GY 9/8 | 5 GY 7/10 |
| Stolon base diameter (mm) | 1.7 | 1.5 | 2.3 | 2.3 |
| Stolons per nursery mother plant | 28.0 | 18.8 | 25.5 | 22.5 |
| Venation | | | | |
| pattern | pinnate | pinnate | pinnate | pinnate |
| color | 10 GY 7/8 | 5 GY 8/8 | 2.5 GY 8/9 | 7.5 G 8/7 |

Diseases and pest reaction:

'Mojave' is moderately resistant to powdery mildew (*Sphaerotheca macularis*), *Verticillium* wilt (*Verticillium dahliae*), and common leaf spot (*Ramularia tulasnei*). It is moderately susceptible to Anthracnose crown rot (*Colletotrichum acutatum*), and is highly susceptible to *Phytophthora* crown rot (*Phytophthora cactorum*) (Table 2 ). When treated properly, it has tolerance to two-spotted spider mites (*Tetranychus urticae*), equal to that for the comparison cultivars. 'Mojave' is tolerant to strawberry viruses encountered in California.

TABLE 2.

Disease resistance scores for 'Mojave' and three comparison cultivars. *Phytophthora* and *Verticillium* scores were obtained in evaluations conducted between 2004-2006; *Colletotrichum* was evaluated between 2005-2006.

| Genotype | *Phytophthora* Resistance Score (5 = best) | *Verticillium* Resistance Score (5 = best) | *Colletotrichum* Resistance Score (5 = best) |
|---|---|---|---|
| 'Camarosa' | 3.06 | 3.08 | 3.1 |
| 'Ventana' | 2.06 | 2.89 | 2.7 |
| 'Palomar' | 2.81 | 4.14 | 3.0 |
| 'Mojave' | 2.31 | 3.75 | 2.7 |

Flowering, fruiting, fruit, and production characteristics:

'Mojave' is similar to other California short-day strawberry cultivars (e. g. 'Ventana', 'Camarosa', and 'Palomar') in that it will flower over an extended period and into spring or summer, given appropriate local temperature and horticultural conditions. With very early plantation establishment (before October 1 in California), 'Mojave' produces fruit as early as 'Ventana' and 'Palomar', and earlier than 'Camarosa', with similar seasonal productivity to 'Ventana'. With later plantation establishment 'Mojave' initiates fruit later than 'Ventana', and is similar in production timing to 'Camarosa' and 'Palomar', with slightly lower seasonal productivity than 'Ventana'. Comparative statistics for flower and fruit characteristics near mid-season are given for the four cultivars in Table 4. The primary flowers for 'Mojave' are smaller than 'Ventana' and 'Camarosa', with a calyx that is usually larger than the corolla on primary fruit, and much smaller than 'Palomar'. The calyx for 'Mojave' varies in position, but frequently has a slight indent later in the season. The fruit shape for 'Mojave' can vary but is larger than the comparison cultivars, and is typically a short to medium and very symmetric conic. It is easily distinguished by fruit shape from 'Camarosa' (shortened and flattened conic), or 'Ventana' (medium symmetrical conic), and 'Palomar' (short symmetrical conic). External and internal fruit color for 'Mojave' is distinctly darker than the comparison cultivars (Table 3). Achenes vary from yellow to dark red, and are even with the fruit surface or slightly indented.

'Mojave' has been tested under a variety of cultural regimes, and optimal performance is obtained when nursery treatments and nutritional programs similar to those of 'Camarosa', 'Ventana', and 'Palomar' are used. In general, plants of 'Mojave' are equally vigorous as 'Camarosa' although 'Mojave' initiates growth more rapidly after transplant. 'Mojave' is less vigorous than 'Ventana', with very early season planting, but more vigorous than 'Palomar'. 'Mojave' retains excellent fruit quality in summer planting systems.

When treated with appropriate planting regimes, 'Mojave' has larger fruit and produces individual-plant yields greater than that of 'Camarosa'. It produces similar quantities of fruit per plant, but develops larger and higher quality fruit than 'Ventana' (Table 5 ). Commercial appearance ratings have been equal to or better than those for all of the comparison cultivars, and are substantially larger than 'Camarosa' and 'Ventana'. 'Mojave' produces a larger fraction of marketable fruit than any of the comparison cultivars. Fruit for 'Mojave' is slightly less firm than fruit from 'Ventana', and much less firm than the other comparison cultivars. Subjectively, 'Mojave' has outstanding flavor. The fruit will be exceptional for both fresh market and processing, and will be useful for home gardening purposes.

TABLE 3

Foliar and fruit color characteristics for 'Mojave' and three comparison cultivars.

| Color | Cultivar | | | |
|---|---|---|---|---|
| Character | 'Camarosa' | 'Ventana' | 'Palomar' | 'Mojave' |
| Leaf color (CIELAB) | | | | |
| Adaxial | | | | |
| L* | | | | |
| mean | 37.1 | 40.0 | 35.2 | 38.0 |
| range | 34.8-41.3 | 33.2-39.2 | 33.7-37.0 | 35.8-42.3 |
| a* | | | | |
| mean | −13.1 | −10.8 | −8.9 | −11.6 |
| range | −11.5--16.8 | −9.1--13.3 | −7.0--11.9 | −8.1--14.1 |
| b* | | | | |
| mean | 16.6 | 15.5 | 11.3 | 15.6 |
| range | 15.3-17.7 | 12.8-19.5 | 9.1-12.3 | 11.4-21.5 |
| Munsell | 5 GY 5/6 | 2.5 GY 4/3 | 5 GY 4/3 | 5 GY 5/6 |
| Abaxial | | | | |
| L*mean | 51.5 | 48.5 | 49.0 | 51.6 |
| range | 48.8-53.4 | 45.6-50.2 | 36.3-50.6 | 47.9-59.3 |
| a*mean | −14.7 | −12.3 | −12.2 | −14.1 |
| range | −13.7--16.5 | −11.3--13.3 | −11.2--13.3 | −13.0--14.9 |
| b*mean | 22.3 | 20.7 | 18.6 | 21.2 |
| range | 19.6-26.2 | 17.6-22.7 | 14.7-22.2 | 18.9-23.7 |
| Munsell | 7.5 GY 8/7 | 7.5 GY 8/7 | 7.5 GY 9/4 | 7.5 GY 9/4 |
| Fruit color (CIELAB) | | | | |
| External | | | | |
| L* | | | | |
| mean | 36.5 | 34.4 | 33.7 | 31.7 |
| range | 33.2-40.0 | 31.7-36.3 | 28.9-36.5 | 28.8-34.6 |
| a* | | | | |
| mean | 33.3 | 33.6 | 34.4 | 36.0 |
| range | 28.6-39.3 | 25.9-38.7 | 24.3-39.7 | 29.7-39.1 |
| b* | | | | |
| mean | 17.9 | 15.8 | 15.4 | 15.0 |
| range | 10.9-26.2 | 10.4-20.9 | 11.5-23.6 | 10.5-19.2 |
| Munsell | 7.5 R 4/11 | 7.5 R 5/13 | 5 R 3/7 | 5 R 3/7 |
| Internal | | | | |
| L* | | | | |
| mean | 53.7 | 52.4 | 48.4 | 52.5 |
| a* | | | | |
| range | 44.2-60.9 | 48.6-57.8 | 42.1-54.9 | 49.7-56.4 |
| mean | 29.6 | 28.8 | 24.7 | 23.2 |
| range | 24.8-33.8 | 23.9-33.9 | 21.1-29.0 | 17.3-40.0 |
| b* | | | | |
| mean | 26.3 | 23.7 | 20.2 | 21.5 |
| range | 21.4-30.1 | 18.1-27.5 | 18.2-23.8 | 19.0-24.1 |
| Munsell | 7.5 R 5/13 | 5 R 5/13 | 7.5 R 6/12 | 5 R 6/11 |
| Achene color Munsell | 2.5 Y 7/10 | 10 Y 8/11 | 7.5 R 8/12 | 7.5 Y 8/12 |

TABLE 4

Flower and fruit characteristics for 'Mojave' and three comparison cultivars.

| | Cultivar | | | |
|---|---|---|---|---|
| Character | 'Camarosa' | 'Nentana' | 'Palomar' | 'Mojave' |
| Petal number | | | | |
| mean | 5.7 | 6.2 | 5.7 | 5.6 |
| range | 5-8 | 5-8 | 5-6 | 5-7 |

TABLE 4-continued

Flower and fruit characteristics for 'Mojave' and three comparison cultivars.

| Character | Cultivar 'Camarosa' | 'Nentana' | 'Palomar' | 'Mojave' |
|---|---|---|---|---|
| Petal shape | | | | |
| apex | truncate to slightly obtuse | truncate to slightly obtuse | truncate to slightly obtuse | truncate to slightly obtuse |
| base | attenuate | attenuate | attenuate | attenuate |
| margin | entire | entire | entire | entire |
| Petal length (mm) | | | | |
| mean | 14.2 | 15.1 | 18.3 | 15.5 |
| range | 13-16 | 14-17 | 15-21 | 14-16 |
| Petal width (mm) | | | | |
| mean | 14.8 | 16.9 | 18.2 | 15.2 |
| range | 13-16 | 16-19 | 15-22 | 14-17 |
| Flower position (relative to foliage) | most even some exposed | even to exposed | even to exposed | even to exposed |
| Calyx diam.(mm) | | | | |
| mean | 48.1 | 45.2 | 57.5 | 36.1 |
| range | 40-52 | 42-52 | 51-61 | 28-45 |
| Corolla diam.(mm) | | | | |
| mean | 37.4 | 39.7 | 44.4 | 35.0 |
| range | 32-44 | 38-42 | 42-47 | 30-40 |
| Sepal length (mm) | | | | |
| mean | 20.6 | 19.7 | 23.5 | 14.3 |
| range | 16-25 | 19-22 | 19-28 | 12-16 |
| Sepal width (mm) | | | | |
| mean | 11.5 | 9.8 | 11.7 | 6.2 |
| range | 10-13 | 8-11 | 10-13 | 5-8 |
| Sepal color (Munsell) | 7.5 GY 5/7 | 2.5 GY 8/9 | 7.5 GY 7/9 | 5 GY 6/8 |
| Pedicel length (mm) | | | | |
| mean | 229 | 259 | 183 | 238 |
| range | 220-240 | 230-290 | 150-210 | 190-290 |
| Pedicel diameter (mm) | | | | |
| mean | 3.1 | 4.3 | 3.7 | 4.8 |
| range | 2-4 | 3-5 | 3-5 | 4-6 |
| Pedicel color | 2.5 GY 6/8 | 2.5 GY 9/8 | 5 GY 8/8 | 7.5 GY 8/7 |
| Fruit shape | | | | |
| Fruit length (mm) | | | | |
| mean | 48.7 | 50.5 | 49.9 | 50.1 |
| range | 43-53 | 45-60 | 43-55 | 45-55 |
| Fruit width (mm) | | | | |
| mean | 40.7 | 45.2 | 44.4 | 44.4 |
| range | 37-51 | 41-53 | 38-55 | 40-52 |
| Length/ width ratio | 1.21 | 1.12 | 1.13 | 1.13 |

TABLE 4-continued

Flower and fruit characteristics for 'Mojave' and three comparison cultivars.

| Character | Cultivar 'Camarosa' | 'Nentana' | 'Palomar' | 'Mojave' |
|---|---|---|---|---|
| range | 1.0-1.4 | 1.0-1.2 | 1.0-1.3 | 1.0-1.3 |
| subjective | Obovate-flat | Medium conic | Short conic | Short-Medium conic |
| Primary/secondary fruit comparison | | | | |
| size (subjective) | 40-60% | 50-60% | 50-60% | 50-60% |
| shape | similar | similar shape | similar shape | similar shape |
| shape, more conic | | | | |
| Extent/size of hollow core | small-absent | Small | small-absent | small-absent |
| Calyx | | | | |
| position | indented-neck | even-reflexed | even-indented | even-indented |
| size relative to fruit | equal or less than fruit diameter | equal or less than fruit diameter | equal or greater than fruit diameter | equal or greater than fruit diameter |
| Seed position | indented-extruded | even-extruded | even-indented | even-indented |
| Adherence of Calyx to Fruit | Weak | Inter-mediate | Weak | Weak |

Flower and plant measurements obtained on Apr. 3, 2008; fruit measurements obtained between May 10-20, 2008.

TABLE 5

Performance of 'Mojave' and three comparison cultivars evaluated in Watsonville, CA between 2008-9. All plants for these trials were harvested from a commercial nursery near Macdoel, CA between October 15-16, and transplanted after 6-7 days to supplemental storage. Fruit harvest was initiated in early April and continued through the last week of August. (52" 2-row beds, 17,300 plants/acre).

| Item | Yield (g/plant) | Appearance Score (5 = best) | Fruit Size (g/fruit) | Firmness |
|---|---|---|---|---|
| 'Camarosa' | 2,137 | 2.7 | 28.6 | 10.1 |
| 'Ventana' | 2,616 | 3.0 | 33.3 | 9.8 |
| 'Palomar' | 2,667 | 3.7 | 34.1 | 10.4 |
| 'Mojave' | 2,271 | 3.8 | 36.1 | 9.5 |

What is claimed is:

1. A new and distinct cultivar of strawberry plant having the characteristics substantially as described and illustrated herein.

* * * * *